United States Patent [19]

Gibbons

[11] 4,032,321
[45] June 28, 1977

[54] N,N-DIALKYL-N'-(SUBSTITUTED-5-ISOTHI-OAZOLYL)-N'-ACYLUREAS AS HERBICIDES

[75] Inventor: Loren Kenneth Gibbons, Medina, N.Y.

[73] Assignee: FMC Corporation, Philadelphia, Pa.

[22] Filed: June 18, 1976

[21] Appl. No.: 697,454

[52] U.S. Cl. .............................. 71/90; 260/306.8 A
[51] Int. Cl.² ...................................... C07D 275/02
[58] Field of Search ................ 260/306.8 A; 71/90

*Primary Examiner*—R. J. Gallagher
*Attorney, Agent, or Firm*—Harrison H. Young, Jr.; Henry R. Ertelt

[57] ABSTRACT

A new class of herbicidal compounds consisting of N,N-dialkyl-N'-(substituted-5-isothiazolyl)-N'-acylureas in which the 3-substitutent on the isothiazole moiety consists of alkyl, alkoxy, alkylthio, alkylsulfinyl, alkylsulfonyl, alkylamino, and dialkylamino, and the 4-substituent on the isothiazole moiety consists of cyano, alkoxycarbonyl, and nitro; and in which the nitrogen atom of the N,N-dialkylurea to which the isothiazolyl moiety is bonded, is also bonded to an acyl moiety, exhibits outstanding preemergence and postemergence herbicidal activity, controlling effectively the growth of a wide spectrum of grassy and broadleaved plant species. The synthesis of members of this class is described in detail and the utility of representative compounds is exemplified.

6 Claims, No Drawings

N,N-DIALKYL-N'-(SUBSTITUTED-5-ISOTHIAZOLYL)-N'-ACYLUREAS AS HERBICIDES

This invention describes novel herbicidal compounds, new herbicidal compositions, and new methods for preventing and destroying undesired plant growth by post-emergence and preemergence application of said new and useful herbicidal compositions to the locus where control is desired. Effective control of the growth of a variety of grassy and broad-leaved plant species is obtained. At herbicidally effective levels of application, some compounds of the invention show selectivity favorable to corn and related species. The herbicidal compositions may be applied and utilized by commonly accepted methods.

Herbicidal (5-isothiazolyl)urea compounds having a cyano, carboxamide or alkoxycarbonyl group in the 4-position are described in the patent literature. See, for example, Belgian Pat. No. 817,903 and published French Application 2,132,191 for compounds in which the 3-substituent of the isothiazole ring is alkyl. Copending applications Ser. No. 697,449 Ser. No. 697,457 and Ser. No. 697,458 filed of even date herewith, describe (5-isothiazolyl)ureas where the 3-substituent on the isothiazole ring is amino, alkoxy, substituted thio, sulfinyl, or sulfonyl; Ser. No. 697,455 describes (5-isothiazolyl)-ureas where the 4-substituent is nitro and Ser. No. 697,456 describes variously substituted (5-isothiazolyl)formamidines also filed of even date herewith. It has now been found that excellent herbicidal activity is obtained by having present, on the nitrogen bearing the isothiazolyl moiety, an alkanoyl moiety. Thus, in one aspect of this invention, novel herbicidal compounds contain an isothiazole ring having the following classes of substituents: on the 3-position, an alkyl, alkoxy, substituted amino, alkylthio, alkylsulfinyl, or alkylsulfonyl; on the 4-position, a cyano, alkoxycarbonyl, or nitro group; and on the 5-position an N'-acyl-N,N-dialkylurea.

One group of herbicidal compounds in accordance with this invention has the following structure (on which the numbering of the various positions of the isothiazole ring is also indicated):

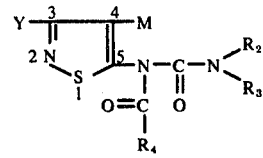

wherein
$R_2$ and $R_3$ are lower alkyl or taken together form a divalent radical which may also contain a hetero atom;
M is cyano, carboxamido, alkoxycarbonyl, or nitro group;
Y is alkyl, alkoxy, alkylthio, alkylsulfinyl, alkylsulfonyl, alkylamino, dialkylamino or a cyclic alkyleneimino group; and
$R_4$ is an alkyl, aryl, or aralkyl group.

The alkyl and cycloalkyl groups preferably have less than 10 carbon atoms. Examples of alkyl groups are methyl, ethyl, propyl, isopropyl, isobutyl, sec-butyl, tert-butyl, 2-pentyl, and so forth. The alkylene groups preferably contain a total of 4 or 5 catenated atoms, no more than one of which is oxygen, sulfur or nitrogen. In the most preferred compound, $R_2$ and $R_3$ are methyl, $R_4$ and Y are alkyl, and M is cyano.

The compounds of this invention may be prepared, for example, by the following reaction sequence:

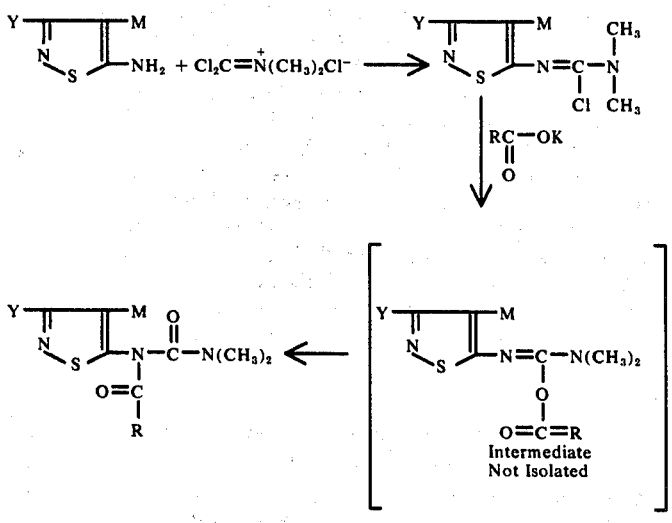

In the descriptions which follow, all temperatures are in degrees centigrade. All reduced pressures not otherwise designated are pressures normally attainable using a water aspirator.

EXAMPLE I

N'-(4-Cyano-3-isopropyl-5-isothiazolyl)-N,N-dimethyl-N'-(2-methylpropanoyl)urea

A. 3-Amino-2-cyano-4-methyl-2-pentenenitrile

A solution of 530.5 g of 3-chloro-2-cyano-4-methyl-2-pentenenitrile in 515 ml of ethanol was added dropwise during 1 hour to a stirred solution of 2,400 ml of concentrated ammonium hydroxide in 1,560 ml of ethanol while maintaining the reaction mixture at 35°–40° with an ice-water bath. The reaction mixture was stirred for 3.5–4 hours and was poured into 6.5 liters of ice and water. The mixture was stirred until all the ice had melted (approximately 30 minutes). The precipitate was collected by filtration. The filter cake was washed with two 1500-ml portions of water and air-dried on the filter. After the drying the 400 g of 3-amino-2-cyano-4-methyl-2-pentenenitrile, mp 182°–184°, was used in the next synthesis step without further purification.

B. 3-Amino-2-cyano-4-methyl-2-pentenethioamide

A mixture of 400 g of 3-amino-2-cyano-4-methyl-2-pentenenitrile (from part A), 400 ml of pyridine and 300 g of triethylamine was stirred and heated to 40° C and the steam bath removed. Gaseous hydrogen sulfide was passed through the solution at a rate sufficient to maintain the reaction temperature at 45°–50° until a total of 125 g had been added (2.25 hours). The solution was stirred for an additional 1–1.5 hours. At this time, the reaction mixture had cooled to 30°. The reaction mixture was poured into a stirred mixture of 4100 ml of water, 2050 ml of ice and 770 ml of ethanol. The mixture was stirred for 1 hour and filtered. The filter cake was slurried with 2100 ml of water and again filtered. The 444.3 g of air-dried solid, 3-amino-2-cyano-4-methyl-2-pentenethioamide, mp 110.5°–112.5°, was used in the next synthesis reaction without further purification.

C. 5-Amino-4-cyano-3-isopropylisothiazole

To a stirred mixture of 444.3 g of 3-amino-2-cyano-4-methyl-2-pentenethioamide (from part B) and 1315 ml of ethanol were added dropwise 298 g of 30% hydrogen peroxide (containing 89.4 g of active $H_2O_2$) during 1.25 hours. The reaction temperature was maintained at 30°–35° with an ice bath. The reaction mixture was stirred an additional 17.5–18 hours in an ambient temperature water bath. The reaction mixture was poured into 5100 ml of cold water with stirring. The water was cooled in an ice-water bath during addition of the reaction mixture. The mixture was stirred for 1 hour at 5°–10° and filtered. The filter cake was washed with 2 liters of water and allowed to dry on the suction filter. After air-drying over a weekend, 426.5 g of 5-amino-4-cyano-3-isopropylisothiazole, mp 130°–132° was obtained.

D. N'-(4-Cyano-3-isopropyl-5-isothiazolyl)-N,N-dimethylchloroformamidine

A mixture of 142 g of 5-amino-4-cyano-3-isopropylisothiazole and 610 ml of dichloromethane was treated with 138 g of N-(dichloromethylene)-N,N-dimethylammonium chloride. The reaction mixture became warm during addition of the N-(dichloromethylene)-N,N-dimethylammonium chloride and was cooled in an ice-water bath to 31°. The reaction temperature was maintained at 30°–35° for one-half hour after addition was complete. The reaction mixture was then heated under reflux for an additional 44 hours. Nitrogen gas was then passed through the refluxing solution for 5 hours. The reaction mixture was allowed to cool to 15°–20° and filtered. The filter cake was washed with 150 ml of dichloromethane and dried to yield an unidentified white solid, mp 162°, which was discarded. The filtrate was washed with two 100-ml portions of saturated sodium bicarbonate solution, dried over anhydrous magnesium sulfate, filtered, and evaporated to near dryness under reduced pressure. The residue was dissolved in 2250 ml of hot hexane, filtered hot and allowed to cool to room-temperature. The hexane solution was decanted from an oil which separated on cooling. The hexane solution was placed in a cooler overnight. The cold solution was filtered and dried to yield 133.7 g of N'-(4-cyano-3-isopropyl-5-isothiazolyl)-N,N-dimethylchloroformamidine, mp 68°–71°. The ir and nmr spectra were consistent with the assigned structure.

E. Potassium 2-methylpropanoate

A mixture of 8.8 g of 2-methylpropanoic acid and 5.6 g of potassium hydroxide in 25 ml of ethanol was allowed to react for 45 minutes. The solution was diluted to a final volume of 500 ml with diethyl ether. The precipitated salt was collected and dried to yield 9.4 g of potassium-2-methylpropanoate.

F. N'-(4-Cyano-3-isopropyl-5-isothiazolyl)-N,N-dimethyl-N'-(2-methylpropanoyl)urea A mixture of 5 g N'-(4-cyano-3-isopropyl-5-isothiazolyl)-N,N-dimethylchloroformamidine (from part D), 4.8 g of potassium 2-methylpropanate (from part E), 20 ml of dry acetonitrile and a catalytic amount of 2,3,11,12-dibenzo-1,4,7,10,13,16-hexaoxacyclotadeca-2,11-diene (dibenzo-18-crown-6) was allowed to react during 24 hours. The inorganic salts were removed by filtration. The volatile materials were evaporated under reduced pressure. The residue was recrystallized from 150 ml of 70:30 hexane:benzene to yield 3.3 g of N'-(4-cyano-3-isopropyl-5-isothiazolyl)-N,N-dimethyl-N'-(2-methylpropanoyl)urea, mp 127°–129°. The ir and nmr spectra were consistent with the assigned structure. The structure assignment was confirmed by the uv spectrum.

Analysis: Calc'd for $C_{14}H_{20}N_4O_2S$: C, 54.52; H, 6.59; N, 18.17; S, 10.40; Found: C, 54.81; H, 6.69; N, 17.93; S, 10.10.

EXAMPLE II

N'-(Acetyl)-N'-(4-cyano-3-isopropyl-5-isothiazolyl)-N,N-dimethylurea

A mixture of 4.9 g of potassium acetate, and a catalytic amount of 2,3,11,12-dibenzo-1,4,7,10,13,16-hexaoxacyclooctadeca-2,11-diene in 60 ml of acetonitrile was stirred vigorously during 45 minutes. Then 12.8 grams of N'-(4-cyano-3-isopropyl-5-isothiazolyl)-N,N-dimethylchloroformamidine in acetonitrile were added. The reaction mixture stood at ambient temperature for 16 hours. Thin layer chromatographic analysis indicated that the reaction had not gone to completion. The reaction mixture was stirred at ambient temperature for 3 days, at which time thin layer chromatographic analysis indicated the reaction to be complete. The reaction mixture was filtered and the filtrate evaporated, under reduced pressure. The residue was slurried in diethyl ether to give a solid. The solid was collected by filtration, then slurried in water to give 10.8 g of N'-acetyl-N'-(4-cyano-3-isopropyl-5-isothiazolyl)-N,N-dimethylurea; mp 128°–130°. The nmr and the ir spectra were consistent with the assigned structure. The uv spectrum confirmed the structure.

Analysis: Calc'd for $C_{12}H_{16}N_4O_2S$: C, 51.41; H, 5.95; N, 19.99; Found: C, 51.37; H, 5.95; N, 19.80.

Herbicidal activities of the compounds of this invention were demonstrated as follows. In preemergence tests, rows of seeds of lima beans (*Phaseolus lunatus*), corn (*Zea mays*), wild oats (*Avena fatua*), lettuce (*Lac-* tuca sativa), mustard (*Brassica juncea*) and crabgrass (*Digitaria sanguinalis*) were planted in shallow flatbed trays (20 cm × 15 cm × 7.5 cm) containing 5 cm to 7.5 cm of sandy loam soil. Within 24 hours after planting, an aqueous acetone solution of the compound (using sufficient acetone to obtain solution) was sprayed on the soil at a rate equivalent to 8.96 kilograms per hectare, 4.48 kg, 2.24 kg, 0.56 kg, and 0.28 kg/hectare, using a total volume equivalent to 760 liters per hectare. The trays were maintained under normal growing conditions in the greenhouse for about 3 weeks, after which the herbicidal efficacy of the compound was assessed. Individual plant species were examined in comparison with untreated plants. Table 1 lists data collected in preemergence tests with compounds of the present invention.

In postemergence tests, rows of seeds were planted as for preemergence tests and the untreated flats were maintained in the greenhouse until the first trifoliate leaves of the bean plants were unfolding. The test plants were then sprayed with an aqueous acetone solution of the compound as for preemergence tests. The plants were returned to the greenhouse and held under normal growing conditions for about 3 more weeks, after which the herbicidal efficacy of the compound was assessed. Table 2 lists data collected in postemergence tests with compounds of the present invention.

TABLE I

Preemergence Herbicidal Activity of N'-(Substituted 5-isothiazolyl)-N,N-dialkyl-N'-acylureas (Expressed as % Kill at Indicated Rate in kg/hectare)

| Compound of Example | Rate | Lima Beans | Corn | Wild Oats | Lettuce | Mustard | Crabgrass |
|---|---|---|---|---|---|---|---|
| I | 8.96 | 100 | 60 | 100 | 100 | 100 | 95 |
|   | 4.48 | 100 | 0 | 100 | 100 | 100 | 95 |
|   | 2.24 | 100 | 0 | 100 | 100 | 100 | 95 |
|   | 1.12 | 90 | 0 | 100 | 100 | 100 | 95 |
|   | 0.56 | 90 | 0 | 80 | 100 | 100 | 50 |
|   | 0.28 | 95 | 0 | 90 | 100 | 100 | 25 |
| II | 8.96 | 100 | 100 | 100 | 100 | 100 | 100 |
|   | 4.48 | 100 | 100 | 100 | 100 | 100 | 100 |
|   | 2.24 | 100 | 100 | 60 | 100 | 100 | 100 |
|   | 1.12 | 100 | 30 | 60 | 100 | 100 | 50 |
|   | 0.56 | 100 | 0 | 50 | 100 | 100 | 40 |
|   | 0.28 | 75 | 0 | 0 | 100 | 100 | 30 |

TABLE II

Postemergence Herbicidal Activity of N'-(Substituted 5-isothiazolyl)-N,N-dialkyl-N'-acylureas (Expressed as % Kill at 8.96 kg/hectare)

| Compound of Example | Lima Beans | Corn | Wild Oats | Lettuce | Mustard | Crabgrass |
|---|---|---|---|---|---|---|
| I | 100 | 100 | 100 | 100 | 100 | 100 |
| II | 100 | 100 | 100 | 100 | 100 | 100 |

For herbicidal application, the compounds of this invention may be utilized in diverse formulations including the agricultural adjuvants and agricultural carriers, i.e. those materials normally employed to facilitate the dispersion of active ingredients in agricultural applications, recognizing the fact that the formulation and mode of application of a toxicant may affect the activity of the material in a given application. Thus, a compound of this invention may be formulated as a granule of relatively large particle size, as a wettable powder, as an emulsifiable concentrate, as a solution, or as any of several other known types of formulations, depending on the desired mode of application.

Granular formulations are particularly useful for aerial distribution or for penetration of a canopy of foliage. Useful granular formulations may be of several types. Impregnated granules are those wherein the active ingredient is applied to large particles of an absorbent carrier, such as an attapulgite or kaolin clay, corncobs, expanded mica, and so forth, normally in the form of a solution in a solvent. Surface-coated granules may be produced by spraying the molten active ingredient onto the surface of a generally non-absorbent particle or by spraying on a solution of active ingredient in a solvent. The core may be water-soluble such as a prilled fertilizer, or insoluble such as sand, marble chips or coarse talc. Particularly useful is a granule wherein a wettable powder is applied as a surface coating to a sand or other insoluble particle such that the wettable powder may be dispersed on contact of the granule with moisture. Granules may be produced by agglomeration of dusts or powders by compaction rollers, by extrusion through a die or by use of a granulating disc. Granular formulations may vary widely in concentration, with useful formulations containing as little as 0.5% or as much as 95% of active ingredient.

Wettable powders, also useful formulations for both pre- and postemergence herbicides, are in the form of finely divided particles which disperse readily in water or other dispersants. The wettable powder is ultimately applied to the soil or to the undesired plant growth either as a finely divided dry material or as an emulsion in water or other liquid. Typical carriers for wettable powders include fuller's earth, kaolin clays, silicas and other highly absorbent, readily wet inorganic diluents. Wettable powders normally are prepared to contain about 5% to 80% of active ingredient, depending on the absorbency of the carrier, and usually also contain a small amount of a wetting, dispersing or emulsifying agent to facilitate dispersion. For example, a useful wettable powder formulation contains 80.8 parts of N'-(4-cyano-3-isopropyl-5-isothiazolyl)-N,N-dimethyl-N'-(2-methyl-propanoyl)urea, 17.9 parts of palmetto clay, and 1.0 part of sodium lignosulfonate and 0.3 part of sulfonated aliphatic polyester as wetting agents.

Other useful formulations for herbicidal applications are the emulsifiable concentrates, which are homogeneous liquid or paste compositions dispersible in water or other dispersant, and may consist entirely of a compound of this invention with a liquid or solid emulsifying agent, or may also contain an agriculturally acceptable liquid carrier, such as xylene, heavy aromatic naphthas, isophorone and other nonvolatile organic solvents.

Typical wetting, dispersing or emulsifying agents used in agricultural formulations include, for example, the alkyl and alkylaryl sulfonates and sulfates and their sodium salts; polyethylene oxides; sulfonated oils; fatty acid esters of polyhydric alcohols; and other types of surface-active agents, many of which are available in commerce. The surface-active agent, when used, normally comprises from 1% to 15% by weight of the herbicidal composition.

These formulations may be applied without further dilution or as dilute solutions, emulsions or suspensions in water or other suitable diluent. The compositions may be applied to the area wherein control is desired by spraying onto the undesired vegetation or onto the surface of the soil in the case of liquid compositions or by distribution from mechanical equipment in the case of solids. The surface-applied material may also be blended into the upper layer of soil by cultivation, or left as applied, as is appropriate to gain the optimum results with the particular treatment.

The active herbicidal compounds of this invention may be formulated and/or applied with insecticides, fungicides, nematicides, plant regulators, fertilizers, and other agricultural chemicals. In applying the active compounds of this invention, whether formulated alone or with other agricultural chemicals, an effective amount and concentration of isothiazolyl compound is of course employed.

It is apparent that various modifications may be made in the formulation and application of the novel compounds of this invention, without departing from the inventive concept herein, as defined in the following claims.

I claim:

1. A substituted isothiazolylurea of the formula:

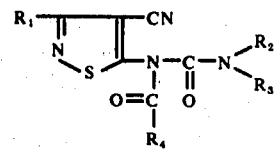

in which $R_1$, $R_2$, $R_3$ and $R_4$ are straight or branched alkyls of 1 to 4 carbons.

2. The compound of claim 1 in which $R_2$ and $R_3$ are methyl.

3. The compound of claim 1 which is N'-(4-cyano-3-isopropyl-5-isothiazolyl)-N,N-dimethyl-N'-(2-methylpropanoyl)urea.

4. The compound of claim 1 which is N'-(acetyl)-N'-(4-cyano-3-isopropyl-5-isothiazolyl)-N,N-dimethylurea.

5. An herbicidal composition comprising an herbicidally effective amount of a compound of claim 1 in admixture with an agriculturally acceptable extender.

6. A method of preventing and destroying plant growth which comprises applying to the locus to be protected an herbicidally effective amount of a compound of claim 1.

* * * * *

UNITED STATES PATENT AND TRADEMARK OFFICE
CERTIFICATE OF CORRECTION

PATENT NO. : 4,032,321

DATED : June 28, 1977

INVENTOR(S) : Loren Kenneth Gibbons

It is certified that error appears in the above-identified patent and that said Letters Patent are hereby corrected as shown below:

Cover page in the title, second line, "OAZOLYL)-N'-ACYLUREAS AS" should read --AZOLYL)-N'-ACYLUREAS AS--; cover page in the Abstract, second column line 2, "3-substitutent" should read --3-substituent--; line 3, "oazole" should read --azole--. Column 1, in the title, second line, "OAZOLYL)-N'-ACYLUREAS" should read --AZOLYL)-N'-ACYLUREAS--. Column 4, line 24, "-hexaoxacycloc-" should read --hexaoxacyclooc- --.

Signed and Sealed this

Twenty-third Day of December 1980

[SEAL]

Attest:

SIDNEY A. DIAMOND

Attesting Officer

Commissioner of Patents and Trademarks